United States Patent
Crome et al.

(10) Patent No.: US 7,694,674 B2
(45) Date of Patent: Apr. 13, 2010

(54) OXYGEN GENERATOR WITH STORAGE AND CONSERVATION MODES

(75) Inventors: Victor P. Crome, Blue Grass, IA (US); Gary N. Byrd, Donahue, IA (US); Russell F. Hart, Blue Grass, IA (US); Scott R. Sehlin, Bettendorf, IA (US); Tuan Q. Cao, Davenport, IA (US); Courtney Joseph Monzyk, Davenport, IA (US); Timothy P. Raleigh, Long Grove, IA (US); Lyle J. Berkenbosch, Bettendorf, IA (US); Craig L. Schledewitz, Davenport, IA (US)

(73) Assignee: Carleton Life Support Systems, Inc., Orchard Park, NY (US)

( * ) Notice: Subject to any disclaimer, the term of this patent is extended or adjusted under 35 U.S.C. 154(b) by 85 days.

(21) Appl. No.: 11/160,171

(22) Filed: Jun. 12, 2005

(65) Prior Publication Data
US 2006/0062707 A1    Mar. 23, 2006

Related U.S. Application Data

(60) Provisional application No. 60/522,362, filed on Sep. 21, 2004.

(51) Int. Cl.
*A61M 15/00* (2006.01)
*A61M 16/00* (2006.01)
*A62B 7/08* (2006.01)
*A62B 21/00* (2006.01)

(52) U.S. Cl. .......................... 128/202.26; 128/205.12; 128/204.18; 128/205.27; 95/96; 95/97; 95/98; 95/99; 95/100; 95/101; 95/102; 95/103; 95/104; 95/105; 95/106; 96/115; 96/117; 96/130; 96/137; 96/143; 96/144; 96/147; 96/149; 96/153; 55/356; 55/357

(58) Field of Classification Search ................... 96/115, 96/117, 130, 137, 143, 144, 147, 149, 153; 95/96–106; 128/205.12, 204.18, 205.27; 55/356, 357
See application file for complete search history.

(56) References Cited

U.S. PATENT DOCUMENTS 5,099,837 A * 3/1992 Russel et al. ........... 128/204.26

(Continued)

FOREIGN PATENT DOCUMENTS

EP       0 733 397 A       9/1996

(Continued)

OTHER PUBLICATIONS

Supplementary European Search Report, EP Application No. EP 05 79 9566; Oct. 13, 2009.

*Primary Examiner*—Patricia M Bianco
*Assistant Examiner*—Nihir Patel
(74) *Attorney, Agent, or Firm*—Marsteller & Associates, P.C.

(57) ABSTRACT

An electronic controller (16) controls the operation of an electrochemical oxygen generating system (14) producing a desired gas. The product gas is fed to a storage unit (12) or a regulator (28) and pulsing valve (28) controlling the gas flow to a user. A two-stage system (180) combines a low pressure 100 and a high pressure (150) gas generating subsystems. The low pressure subsystem (100) uses IMAT's (106) to pump oxygen from ambient air to generate a low-pressure. The high pressure subsystem (150) uses IMAT's (160) to pump oxygen to high-pressure oxygen storage devices (194).

10 Claims, 6 Drawing Sheets

U.S. PATENT DOCUMENTS

| | | | | |
|---|---|---|---|---|
| 5,498,487 A | * | 3/1996 | Ruka et al. | 429/20 |
| 5,809,999 A | * | 9/1998 | Lang | 128/200.24 |
| 5,855,762 A | * | 1/1999 | Phillips et al. | 205/634 |
| 5,871,564 A | | 2/1999 | McCombs | |
| 5,871,624 A | | 2/1999 | Crome | 204/286 |
| 5,985,113 A | | 11/1999 | Crome et al. | 204/286 |
| 6,024,859 A | * | 2/2000 | Hsu | 205/343 |
| 6,194,335 B1 | | 2/2001 | Crome et al. | 501/103 |
| 6,352,624 B1 | | 3/2002 | Crome et al. | 204/277 |
| 6,450,943 B1 | | 9/2002 | Crome et al. | 600/19 |
| 6,783,646 B2 | * | 8/2004 | Sehlin et al. | 204/279 |
| 2005/0160909 A1 | * | 7/2005 | Meirav | 96/108 |

FOREIGN PATENT DOCUMENTS

| | | |
|---|---|---|
| WO | WO 95/27810 A | 10/1995 |
| WO | WO 99/48595 A | 9/1999 |
| WO | WO 2007/060141 A1 * | 5/2007 |

* cited by examiner

OXYGEN GENERATOR WITH STORAGE AND CONSERVATION MODES

CROSS REFERENCE TO RELATED APPLICATIONS

This application claims the benefit of U.S. Provisional Application Ser. No. 60/522,362, filed Sep. 21, 2004, entitled OXYGEN GENERATOR WITH STORAGE AND CONSERVATION MODES.

BACKGROUND OF THE INVENTION

1. Technical Field

The invention relates to the field of electrochemical gas generators, and more particularly to ceramic oxygen generating systems (COGS) for generating and delivering oxygen to a user.

2. Background Art

There are a variety of ways to generate and deliver substantially pure oxygen for use in medical applications and in the electronic industry, for laser cutting, and in many other applications. Two key areas of use for pure oxygen are breathing purposes in home oxygen therapy (HOT) patients and for aviation crewmembers.

Oxygen can be stored in cylinders at elevated pressures and stored as liquid oxygen in what is commonly called a Dewar. These techniques are of common knowledge and have been utilized for many years.

More recently oxygen can be concentrated or generated real-time using a variety of molecular sieves to separate and concentrate oxygen from a pressurized air source using a pressure swing adsorption process (PSA) or a vacuum pressure swing adsorption (VPSA) process. Oxygen product generated by pressure swing adsorption is low cost and readily available. However, the oxygen concentration on these products is about 90 to 95%.

Even more recently oxygen can be generated using an electrochemical process that ionizes the oxygen molecules at one surface of a ceramic membrane, transports the ions through the membrane, and reforms them as oxygen molecules on the other surface of the membrane by removing the excess electrons from the ions. This type of technology is also known as a ceramic oxygen generating system (COGS).

Oxygen conserving devices that provide a short pulse of oxygen to the user through a nasal cannula at the beginning of inhalation have been widely used for many years to reduce the quantity of supplemental oxygen delivered to patients who suffer from chronic lung disorders while still maintaining an adequate oxygen saturation level in the blood stream. This has been commonly referred to as pulse dosing of oxygen.

This type of oxygen pulse dosing technology has recently been used on aircraft to provide supplemental oxygen to pilots of general aviation aircraft that typically fly at altitudes of up to 32,000 feet. Similarly, oxygen breathing regulators have been used for many years to reduce the amount of oxygen consumed by aerospace crewmembers at various altitudes to minimize the possibility of oxygen toxicity of the user, while providing a minimum level that is a physiologically safe oxygen concentration to prevent the occurrence of hypoxia at higher altitudes. Physiologically safe concentrations of oxygen have been provided by the breathing regulators that entrain aircraft cabin air and add it to the stored or generated oxygen before delivery to the crewmember to lower the concentration to the desired level as a function of atmospheric pressure-altitude. This is most commonly accomplished using the well-known pneumatic injector device. This technique has also been used to dilute the oxygen generated from PSA oxygen concentrators in aircraft to the desired concentration.

If an aircraft is equipped with the PSA oxygen concentrator and cabin pressure of an aircraft is lost above an aircraft altitude of about 30,000 feet, then the purity of the oxygen being generated by the PSA, which is only about 95% Oxygen, does limit the time of exposure that the crewmember can safely stay at the higher altitudes. However, if the aerospace oxygen system is comprised of stored oxygen of 99.5% Oxygen or has a back-up oxygen system (BOS) that contained 99.5% oxygen, then additional aircrew safety can be provided in the event of the loss of cabin pressure at these higher altitudes. However, the use of 99.5% oxygen in either the high-pressure storage or liquid form requires periodic replenishment ranging from daily to weekly periods of time and results in a logistics burden to the user.

The implementation of the PSA oxygen concentrators into aerospace applications has solved the requirement for oxygen on a daily basis, but has had limited acceptance as a supply of oxygen for use after the loss of cabin pressure at the higher altitudes. Currently, only the F-15E aircraft uses a back-up oxygen supply that is automatically filled with 93% oxygen that is generated and stored using a PSA oxygen concentrator with an integral compressor. An emerging limitation to using PSA oxygen concentrators on next generation aircraft is the trend towards the use of more efficient engines with higher bypass ratios that result in less compressed air being available for the PSA oxygen concentrator and other air handling systems on the aircraft. This results in market pressures to minimize or eliminate the use of compressed air from the aircraft engine.

Many aerospace applications need a way to generate oxygen at a purity of greater than 99.5% and store it at an elevated pressure for emergency conditions, while providing a lower concentration for normal flying conditions when the aircraft cockpit is equivalent to a pressure-altitude of less than about 25000 feet. This system needs to be compatible with current aircraft personal equipment that includes oral-nasal masks that can deliver the oxygen at pressures up to about 70 mmHg under certain normal and emergency flying conditions.

Similarly, many home oxygen therapy patients can benefit from an oxygen generator that can deliver oxygen in the home via a pulse-dosing oxygen conserving device using a nasal cannula during, while also storing oxygen in a portable cylinder for temporary use outside the home. This reduces the logistics burden of the home health care provider by eliminating the need to replenish the portable oxygen cylinders after use. Some patients that have sleeping disorders are better served by a continuous flow from the nasal cannula in order to maintain the desired oxygen blood saturation levels while they sleep.

Certain ceramic materials, when subjected to specific conditions, will actively pass oxygen atoms through its matrix. Previous embodiments of this concept have shown that a properly designed ceramic membrane can act as both a means for concentrating 100% oxygen and for pressurizing oxygen to levels suitable for recharging conventional oxygen cylinders.

A basic ceramic oxygen generating system generally consists of one or more temperature controlled ovens which contains ceramic oxygen generating elements. In order to supply enough oxygen for the ceramic elements, air is circulated inside the oven. Since the ceramic elements operate at high temperature (about 700° C.), air has to be heated before inputting to the oven. Heat exchangers are used to preserve the heat and reduce temperature of oxygen-depleted air exhausted from the oven.

Major problems of such a basic COGS described include:
- The ratio of air input flow to oxygen output flow is very high (20 to 1). This high input flow requires having heat exchangers to avoid heat loss or thermal shock to the ceramic elements.
- Heat exchangers efficiency needs to be high to preserve the heat. Therefore, they are expensive.
- To exchange the heat, the oven has to be pressurized to generate a return (oxygen-depleted exhaust) flow. The positive pressure generates thermal leak around openings/cracks on the oven.

Oxygen at high purity levels, high pressures, and high temperatures creates a hazardous environment because it will support vigorous combustion of many conventional materials. Thus, it is very difficult to design a cost-effective pressure vessel capable of holding pure oxygen at high pressures and high temperatures. Previous embodiments of this concept have utilized the ceramic membrane as an initial pressure vessel for the high purity oxygen, until it can be cooled enough for safe transfer to, and storage in, conventional oxygen cylinders.

Using the ceramic membrane as a pressure vessel incites a powerful conflict between maximum operating pressures and the rate of oxygen concentration. The ceramic material is relatively brittle, thereby ill suited for withstanding the tensile stresses associated with internal pressurization. Increasing the wall thickness of the module will lower the material stresses, but it will also lower the module's oxygen concentration rate and operating efficiency.

Ceramic oxygen generating modules such as the Integrated Manifold And Tubes (IMAT) described in U.S. Pat. Nos. 5,871,624; 5,985,113; 6,194,335; 6,352,624; and others have been used in oxygen generating systems. However, in most of the applications, the IMAT's outside surfaces are interfaced with air and oxygen is pumped through the ceramic to the inside cavities (circuit). This design limits the maximum oxygen generating pressure due to high tensile stresses on the ceramic.

While the above cited references introduce and disclose a number of noteworthy advances and technological improvements within the art, none completely fulfills the specific objectives achieved by this invention.

SUMMARY OF INVENTION

In accordance with the present invention, oxygen is pumped from the inside of the IMAT to generate pressure on the outside. Ceramic withstands more stress in compression than tension. Hence, maximum generating pressure can be improved compared to the aforementioned design.

A first embodiment of the present invention includes an electronically controlled unit controlling the operation of an electrochemical oxygen generating system producing a controlled amount and pressure of a desired gas such as oxygen. The output or product gas from the gas generating system is fed either to a storage unit or to a regulator that controls the product gas flow to a user of the purified oxygen or other gas. A pulsing valve may be included with the regulator to further control the amount and flow of the purified oxygen to the user.

A second embodiment of the COGS unit includes a two-stage system that optionally combines two subsystems. One subsystem uses the IMAT's to pump oxygen from ambient air to the inside circuit to generate low-pressure oxygen. The other subsystem uses a second group of IMAT's to pump oxygen from the inside circuit to suitable high-pressure oxygen storage devices.

The advantages of the present invention are:
Same configuration of IMAT's can be used on both subsystems.
IMAT's in production line can be segregated into lower and higher performance and can be used in low pressure or high pressure subsystems. The segregation and utilization will reduce scrapped IMAT's. Therefore, the yield could improve.

The output oxygen purity of the low pressure subsystem of the present invention is very high. Therefore, there is no purging required on the high pressure subsystem.

Another object of the present invention is to eliminate the conflict between maximum operating pressures and the rate of oxygen concentration when using the ceramic membrane as a pressure vessel.

These and other objects, advantages and features of this invention will be apparent from the following description taken with reference to the accompanying drawings, wherein is shown the preferred embodiments of the invention.

BRIEF DESCRIPTION OF DRAWINGS

A more particular description of the invention briefly summarized above is available from the exemplary embodiments illustrated in the drawing and discussed in further detail below. Through this reference, it can be seen how the above cited features, as well as others that will become apparent, are obtained and can be understood in detail. The drawings nevertheless illustrate only typical, preferred embodiments of the invention and are not to be considered limiting of its scope as the invention may admit to other equally effective embodiments.

DETAILED DESCRIPTION

So that the manner in which the above recited features, advantages, and objects of the present invention are attained can be understood in detail, more particular description of the invention, briefly summarized above, may be had by reference to the embodiment thereof that is illustrated in the appended drawings. In all the drawings, identical numbers represent the same elements.

Figure 1:
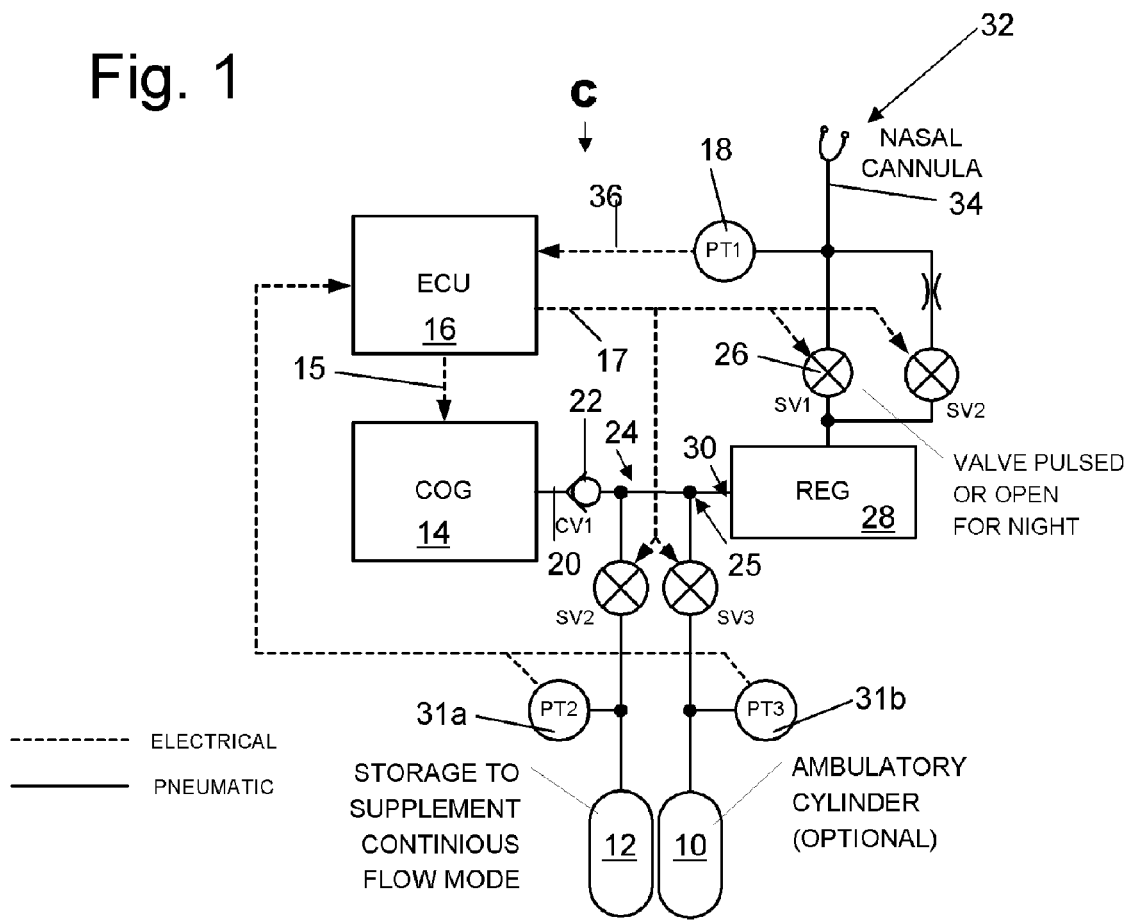
FIG. 1 is an electrical and pneumatic block diagram of the present invention for generating and storing the desired gas adapted for general home oxygen therapy uses.
Figure 2:
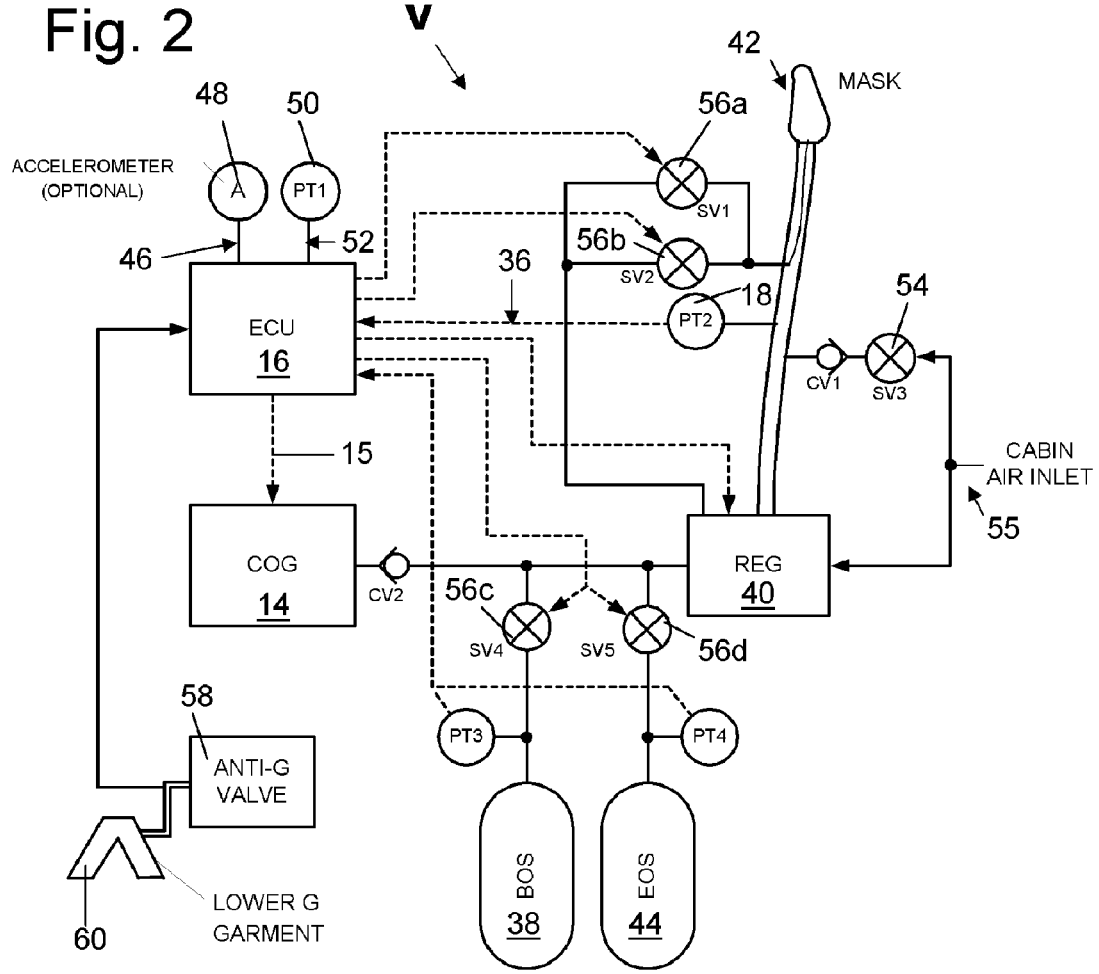
FIG. 2 is an electrical and pneumatic block diagram of the present invention for generating and storing the desired gas adapted for aviation uses.

Referring particularly to FIGS. 1 and 2, a first embodiment of the present invention includes an electronically controlled unit 16 controlling the operation of an electrochemical oxygen generating system or COGS 14 that produces a controlled amount and pressure of a desired gas such as oxygen. The output or product gas from the gas generating system 14 is fed either to a storage unit 12 or to a regulator 28 that controls or governs the product gas flow to a user of the purified oxygen or other gas. A pulsing valve 26 may be included with the regulator 28 to further govern the amount and flow of the purified oxygen to the user.

The above identified problems for home oxygen therapy (HOT) uses can be simultaneously satisfied by a COGS C that generates and stores the oxygen in a cylinder or other suitable storage vessel 10 for portable use and also has the option of filling another storage vessel 12 for activation and use during sleep, when constant oxygen flow is more effective for those patients with sleeping disorders such as sleep apnea. The present invention helps to reduce the size, weight, and power of the COGS C while providing the adequate flow rates for the patient scenarios mentioned above.

An example of the potential savings is given in the following analysis. A home-healthcare patient that may require a continuous 3 lpm dosage at night may only require 1 lpm during the day. In this scenario the total oxygen usage/day is calculated as shown below.

3 lpm×60 min/hour×8 hours+1 lpm×60 min/hour×16 hours=2400 liters

Currently, a typical PSA concentrator would be sized to provide 3 lpm continuously to meet the worst case demand.

A typical electronic pulse dosing system can provide a 6 to 1 savings in gas consumption which results in a daily total oxygen consumption as calculated below.

3 lpm×60 min/hour×8 hours+⅙ lpm×60 min×16 hours=1600 liters

By using a pulse dosing system and storing the extra oxygen produced during the day for use in the continuous flow mode at night the oxygen generation system (PSA or COGS) can be sized to produce 1.11 liters per minute (1600 liters/1440 minutes/day). Thus the oxygen supply system can be sized to provide less than half the gas required by conventional systems while still providing continuous peak flows at night.

Such a schematic for a system C suitable for HOT uses is shown in FIG. 1. The COGS C includes a ceramic oxygen generator (COG) unit 14 that electrochemically extracts oxygen from the surrounding air and delivers it at elevated pressures through a gas line 20 having a flow valve 22. An optional ambulatory storage cylinder 10 and an optional gas storage vessel 12 for night time continuous-flow mode are connect in fluid flow with a flow path or pipe 24 to a manifold or T junction or junctions 25 having one branch operably connected to valve 22. An electronic control unit (ECU) 16 that controls the system operation is electrically or otherwise operationally connected by connection path 15 to the COG unit 14 and to a pressure transducer (PT1) 18 that senses the patient or user inhalation demand. A valve 26 is commanded open by the ECU 16 at the preferred time and duration. A regulator unit 28 is operably connected in the fluid flow path 30 between the manifold or T junction(s) 25 and an air or gas flow valve 26 that is commanded open by a control signal 17 from the ECU 16 for preferred or selected time and duration. Pressure transducers (or switches) (PT2, PT3) 31a and 31b may be used to provide feedback to the ECU 16 on the storage tank 12 and ambulatory cylinder 10 pressures.

Generally, a cannula, mask, or other known oxygen delivery means 32 is in fluid communication with the regulator 28 or valve 26 through tubing path 34 that may optionally feed an input stream to the pressure transducer 18 to provide a feedback signal 36 to the ECU 16.

Alternative embodiments of a system C suitable for uses including HOT may include:
(1) a separate ECU for pulse dosing, which ECU may be detachable so it goes with the cannula, pressure transducer, regulator, or ambulatory cylinder; and,
(2) the ambulatory and supplementary storage connectors may be designed to allow for automatic sourcing from the supplementary storage upon remounting the ambulatory cylinder 10 to the unit.

Referring particularly to FIG. 2, an alternative embodiment of the present invention provides a solution to the problems associated with the set of conditions for aviation oxygen scenarios. The present aviation oxygen system V is comprised of a ceramic oxygen generator unit 14 capable of delivering a minimum of 99.5% oxygen at several hundred pounds per square inch pressure, a first oxygen storage vessel or tank 38, an oxygen-conserving regulator 40, and a known oral-nasal type of aircrew oxygen mask 42 preferably equipped with oxygen conserving features.

The aviation embodiment of the ceramic oxygen generating (COGS) V generates the oxygen without the need for a separate or external pressurized air supply from the aircraft. Preferably, the device is robust enough to deliver it at 500 psig or higher in order to reduce the size of the storage vessel 38 and eliminate the need for an interim compressor (not shown). Such a device does exist and is taught in U.S. Pat. No. 5,871,624 and several related subsequent patents. The generator unit 14 is designed to provide sufficient oxygen to the aircrew member(s) using the present oxygen conserving techniques, while also delivering excess oxygen generated to the storage vessel or back-up oxygen system (BOS) 38 or an optional emergency or stand-by storage vessel or system (EOS) 44 at the desired elevated pressure.

Operating Mode of the Regulator

The oxygen-conserving regulator 40 preferably has one or more operating modes. The NORMAL mode utilizes pulse dosing to deliver oxygen only during the initial period of the crewmember's inhalation; thereby conserving oxygen while providing oxygen when it is most effective in the breathing cycle. This results in no reduction of safety, but does result in reduction of oxygen consumption. The stored oxygen is retained for use when higher flows or higher concentrations are needed.

When cabin pressure is lost at higher altitudes that require increasing oxygen concentration, the pulse dosing transitions to longer duration pulses and into a 100% MODE at the higher altitudes, where oxygen is delivered to the crewmember via a demand flow valve that responds to crewmember's demand for breathing gas instead of the pulse dosing mode. This flow can be controlled pneumatically by a known breathing-diaphragm acting through a mechanism, or by a pressure transducer and feedback electronic control circuit acting upon one or more electrically operated flow control valves.

At cabin altitudes above about 40,000 feet, the breathing regulator can also control the flow to deliver the oxygen at elevated breathing pressures to the crewmember to provide pressure breathing for altitude (PBA) to further enhance and maintain the absorption of oxygen by the lungs at these reduced atmospheric pressures.

The regulator 40 responding to an input signal 46 from an optional accelerometer 48 can also provide the oxygen pressure as a function of aircraft acceleration to assist in combating the incapacitating flow of blood from the head at the higher accelerations above about 4 times the normal gravity level. This has been commonly referred to as pressure breathing for G's (PBG). An optional anti-G valve component 58 may be operationally connected to the ECU 16 and other components of the present aviation system V as desired. Additionally, a lower G garment or aviation G suit 60 may be operationally connected to the aviation system V through the anti-G valve 58.

Optionally, a pressure transducer 50 can generate a control signal 52 to the ECU 16. Further, the ECU 16 can be operationally connected to the regulator 40. A flow valve 54 may optionally be placed in the flow path between a cabin air inlet 55 and mask 42. The air flow from the cabin air inlet 55 may also be communicated to the regulator 40 permitting mixing of cabin air with the purified gas product.

Additional controls or valving systems 56a, 56b, 56c, 56d may be operably connected to provide back-up safety control systems for the user.

Two Stage System

A further embodiment of the COGS subunit includes a two-stage system 180 that optionally combines a low pressure 100 and a high pressure 150 gas purifying or generating subsystems. The low pressure subsystem 100 uses the IMAT's 106 to pump oxygen from ambient air to the inside circuit to generate low-pressure oxygen. The other high pressure subsystem 150 uses a second group of IMAT's 160 to pump oxygen from the inside circuit to suitable high-pressure oxygen storage devices 194.

Low Pressure Subsystem Component

Figure 4:
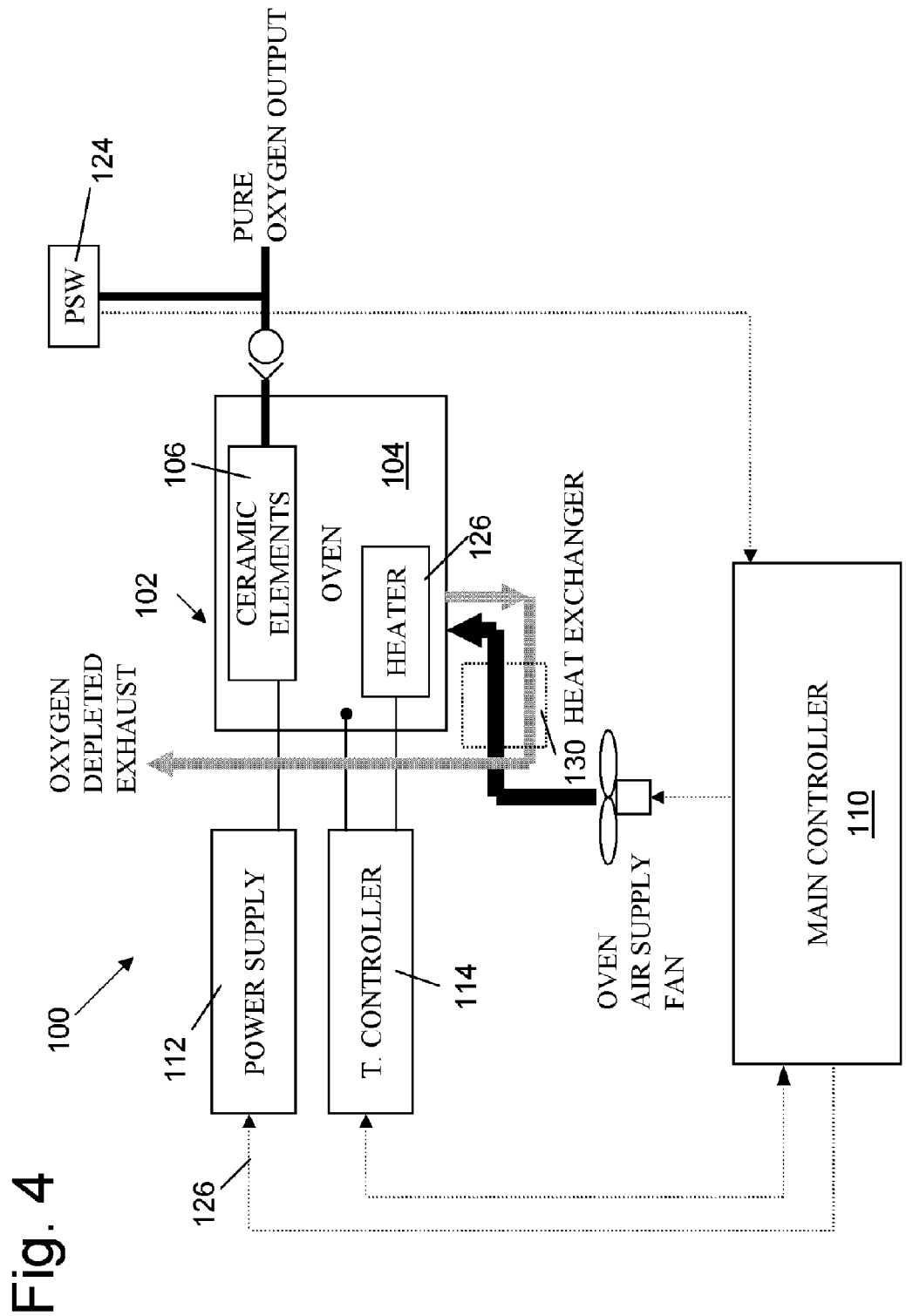
FIG. 4 is an electrical and pneumatic block diagram of the low pressure COGS subsystem of the present invention.
Figure 5:
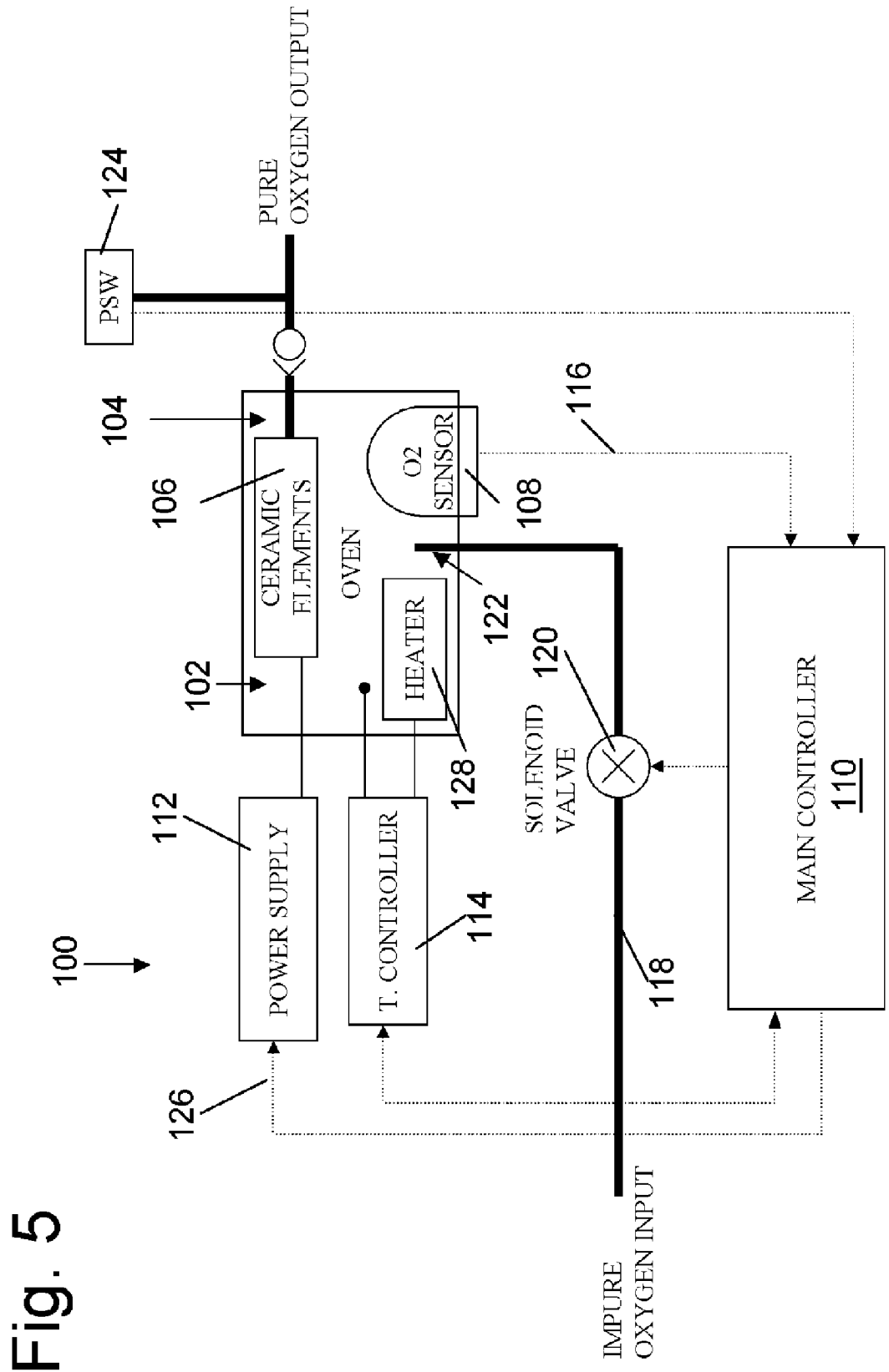
FIG. 5 is an electrical and pneumatic block diagram showing associated components of the low pressure COGS subsystem of the present invention.

Referring particularly to FIGS. 4 and 5, the low pressure subsystem or component 100 of the present invention uses ceramic oxygen generating elements for purifying impure oxygen supplied by other oxygen generating techniques such as pressure swing adsorption (PSA).

The oxygen purifying subsystem 102 generally consists of an oven 104 housing one or more known ceramic oxygen generating elements (ceramic elements) 106, an optional oxygen sensor 108, a controllable impure oxygen input circuit (not shown), a main controller 110, and associated components operably connected, such as a power supply 112, a temperature controller 114, etc. as is shown in FIG. 5.

The temperature controller 114 controls internal oven 104 temperature within an interior chamber during warm-up and during operation. The oven temperature is ramped up to the operating temperature to avoid thermal shock to the ceramic elements 106. The temperature should be controlled to constant operating temperature (about 700° C.).

The oxygen sensor 108 senses oxygen concentration inside the oven 104 and supplies a signal through connection 116 to the main controller 110. The oxygen sensor 108 is generally a known ceramic type (i.e. zirconia) with operating temperature about the same as of the ceramic elements. An automotive oxygen sensor can be a good candidate for use in this application.

The impure oxygen input circuit 118 that is operably connected to the oven 104 includes generally an optional flow restrictor (orifice), a solenoid valve 120, and a high temperature distribution tube 122. The main controller 110 controls the solenoid valve 120 to pulse a restricted oxygen flow into the oven 104. The valve control may be based on an oxygen concentration feed back signal from the oxygen sensor 108. Preferably, the oxygen concentration within the oven 104 is maintained in the range of 15 to 20% of concentration for optimum IMAT operation without losing oxygen to ambient conditions or otherwise degrading performance.

The main controller 110 performs all the control functions. When outlet pressure is less than maximum pressure (indicated by the pressure switch PSW 124), the main controller 110 signals the power supply 112 through connection 126 to apply power to the ceramic elements 106. In the mean time, the main controller 110 controls the oxygen concentration inside the oven 104 to the level below the oxygen concentration of ambient air (20.9%) and above the minimum level for operating the ceramic elements efficiently (15%). The oxygen concentration is preferably controlled between 18-20%.

The low pressure subsystem 100 generally includes other known components such as the oven heater component 128, a heat exchanger 130, fans, tubing, valves, and other items.

The advantages of the low pressure subsystem of the present invention are:
Either no heat exchanger is needed or a lower efficiency heat exchanger is acceptable. The input to output flow ratio is low. Therefore, the input can be preheated during traveling inside the distribution tube.
The operating pressure of the oven 104 need only be held slightly above ambient pressure. Therefore, the heat loss through convection is significantly reduced.
Oxygen concentration inside the oven 104 is controlled to optimize the performance of the ceramic elements 106 without losing oxygen to the ambient.

High Pressure Subsystem Component

Figure 3:
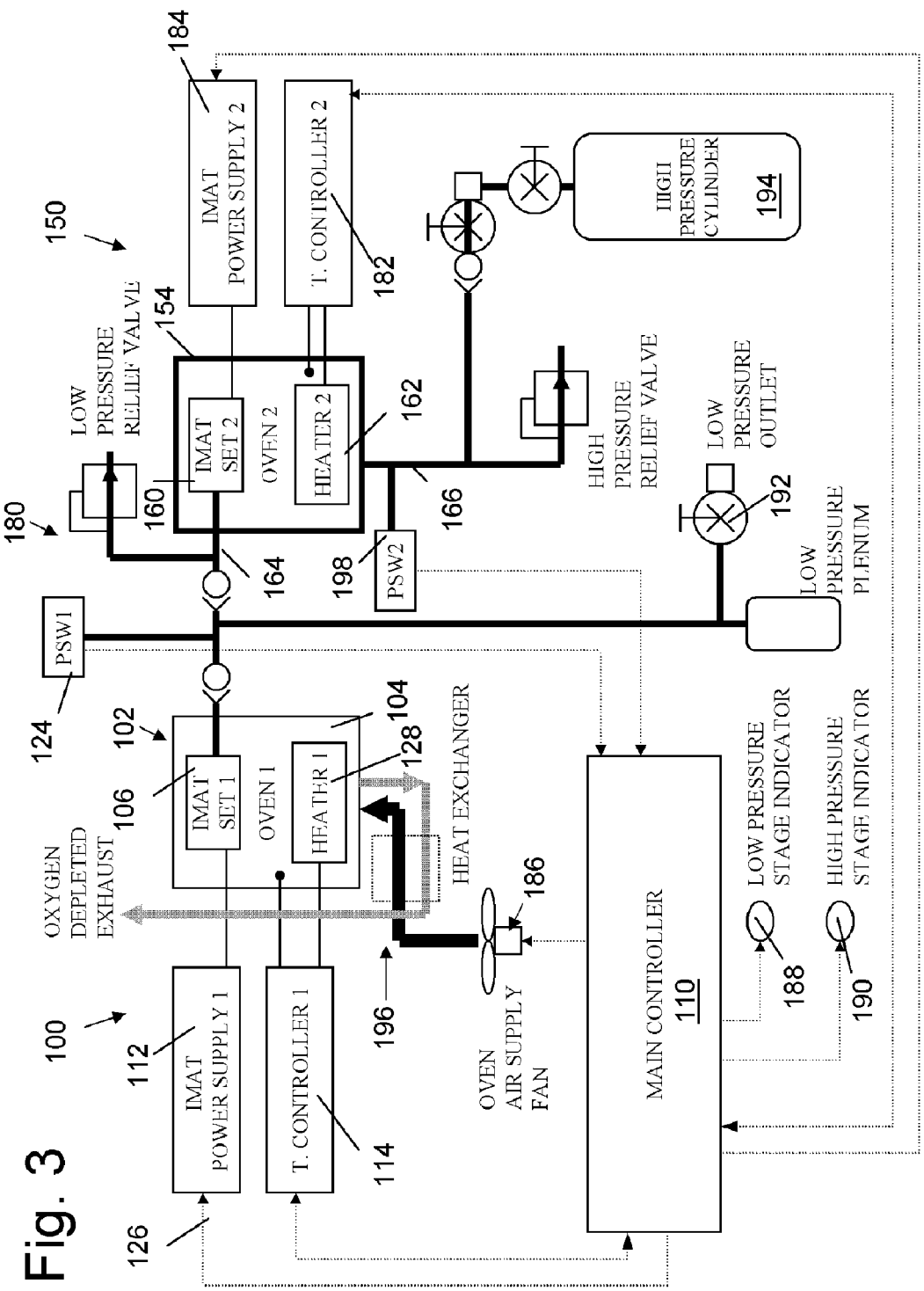
FIG. 3 is an electrical and pneumatic block diagram of the present invention having the low and high pressure subsystems generating the desired gas.
Figure 6:
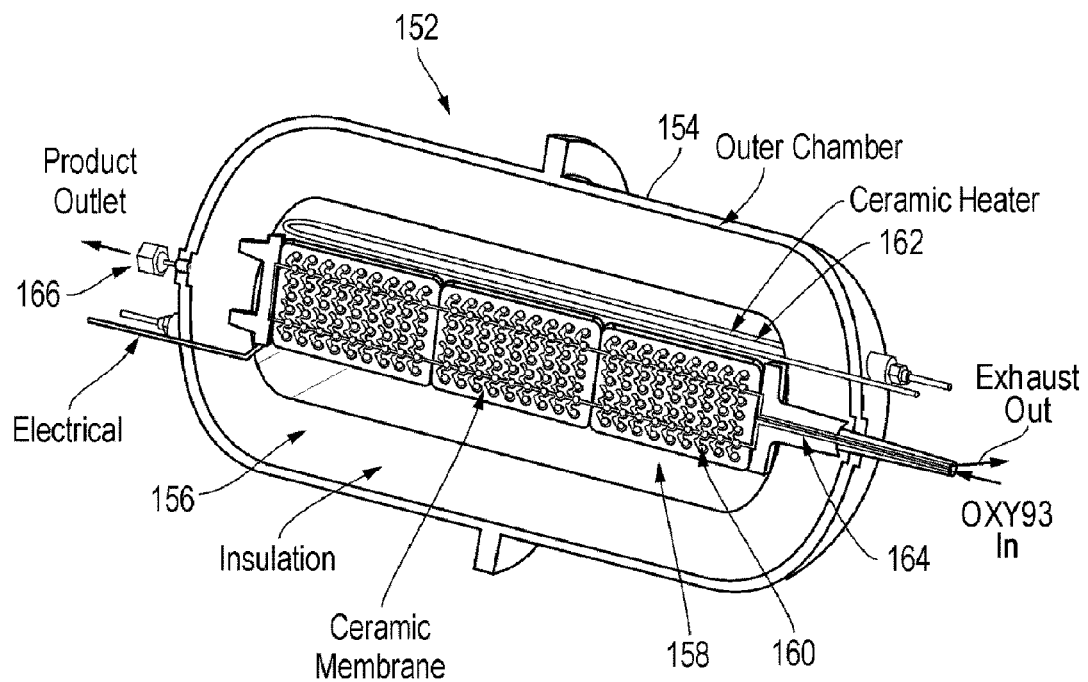
FIG. 6 is a sectional view of the high pressure COGS subsystem of the present invention.
Figure 7:
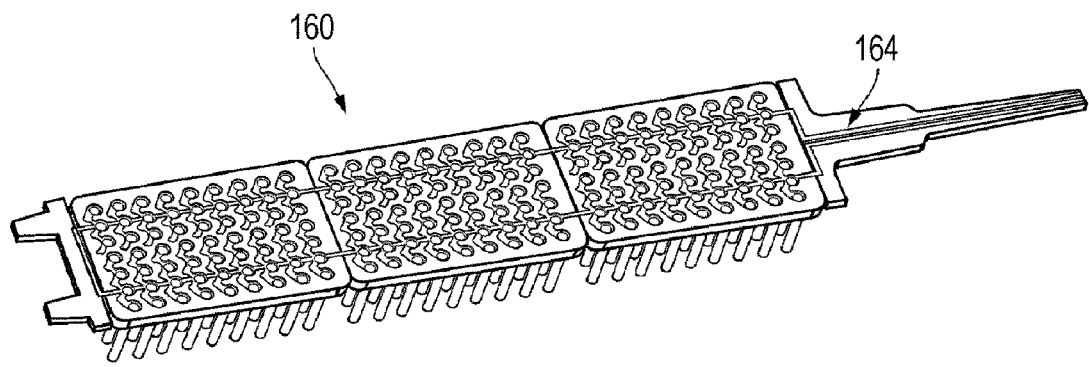
FIG. 7 is a perspective view of the ceramic membrane section or IMAT that may be used in the present invention.

Referring particularly to FIGS. 3, 6 and 7, the high pressure subsystem 150 or component of the present invention subjects the previously described ceramic membrane to compressive forces instead of tensile forces. The ceramic material is approximately fifteen times stronger in compression than it is in tension. Achieving this feat requires finding a way to contain high pressure, high temperature oxygen in a cost-effective pressure vessel 152 better suited for handling tensile forces.

The pressure vessel 152 preferably consists of a metallic outer shell 154 and also acts as an oven. The shell 154 may be lined with a suitable amount of high temperature, non-combustible insulation 156. The purposes of the insulation 156 are to keep the metallic shell 154 relatively cool and to shield the material from potential ignition sources located further inside the interior chamber 158. Keeping the outer shell 154 cool also allows the material to maintain high tensile strength properties, lessens the potential for hazardous interaction with oxygen, and makes it easier to maintain a high-pressure seal between the outer shell 154 and the ceramic membrane 160.

Temperature control of the interior chamber 158 may consist of two separate processes. First, the chamber 158 can be brought up to operating temperature by means of a heat source 162. Preferably, this heat source 162 consists of a non-combustible, high-temperature heating element located inside the chamber 158. Alternative heating methods may include a removable metallic element, a metallic element shielded by a high temperature, non-combustible material, or an externally generated heat source, such as microwave energy routed to the inside of the chamber 158.

Temperature of the chamber 158, while the ceramic membrane 160 is operating, should be controlled, in combination, by adjusting the voltage across the ceramic membrane 160 and by controlled cooling of the outer shell 154 by external means. To lessen the possibility of ignition, the heat source 162 used to bring the chamber 158 up to operating temperature can be disabled or removed while high purity oxygen is present inside the chamber 158.

The preferred embodiment of the high pressure subsystem component 150 provides the inside of the ceramic membrane 160 with concentrated oxygen as a source gas. Thus, the relative composition of the input gas may be pre-selected with reference to the desired product gas in order to reduce operating burden on the ceramic membrane unit during operation.

The use of concentrated or enriched oxygen will lessen the thermal requirements of the system during operation by requiring much less inlet flow than using atmospheric air.

Alternatively, the input gas may be pre-treated such as with a heat exchanger as is well known in the art to reduce the thermal shock on the ceramic membrane 160 when the input gas is introduced into the inlet port 164.

Since safety is a major concern with any application having high-pressure oxygen, a plurality of flow control devices may be used at both the inlet port(s) 164 and product outlet port(s) 166 of the chamber 158 as described to minimize leakage in case of failure of the ceramic membrane 160.

Optionally, the interior chamber 158 may be evacuated or pre-pressurized to improve start-up performance.

The ceramic membrane 160 may be any electrochemical oxygen or gas generating system, such as the flat plate, tube, or honeycomb types of known electrochemical gas generators or solid electrolyte oxygen generating cells.

Combined Subsystems for the Two Stage Ceramic Oxygen Generating System

Referring particularly to the two-stage Ceramic Oxygen Generating System 180 functional diagram of FIG. 3, the present invention includes both the high pressure subsystem 150 and the low pressure subsystem 100 of the present invention.

The two stage system 180 consists of a low-pressure stage (Oven 1) 100 with associated temperature controller 114, IMAT power supply 112 and an oven air supply fan or blower 186, a high-pressure stage (Oven 2) 150 with associated temperature controller 182 and IMAT power supply 184, a main controller 110, and optional input/output and user interfaces or indicators 188 and 190 respectively that are operably connected to the main controller 110. The temperature controllers 114 and 182 can be separate components or a sub-part of the main controller 110.

The two stage system 180 is functionally divided into two subsystems or stages: low-pressure and high-pressure subsystems. The low-pressure subsystem 100 as previously described has heated ambient air or controlled impure oxygen input to the oven 104. This low-pressure subsystem 100 generates low-pressure oxygen (0-100 psig). The low-pressure oxygen product can be supplied to high-pressure subsystem 150 as an input feed stream or output to a low-pressure outlet 192 for usage.

The high-pressure subsystem 180, also previously described, receives an input from the low-pressure subsystem 100. The high-pressure subsystem 180 generates high-pressure oxygen for re-charging high-pressure cylinders 194 (up to 2000 psig).

The low-pressure subsystem 100 consists of an oven 104 with integral heater 128, a temperature controller 114 that can be part of the main controller 110, a set of IMAT's 106 (the number of IMAT's depends on the output requirements), an air input and distribution 196 with heat exchanger 130 and fan 186, and an IMAT power supply 112. The oven 104 for low-pressure stage 100 is thermally designed so that thermal run-away would not occur. The temperature controller 114 controls the operating temperature during normal operation.

The high-pressure subsystem 150 consists of high-pressure sealed oven 152 with oxygen compatible heater 162, a temperature controller 182 (can be part of the main controller), a set of IMAT's 160 (the number depends on the output requirements and the number of IMAT's in the low-pressure subsystem), and an IMAT power supply 184.

The ratio between numbers of IMAT's used in the two stages depends on maximum allowable current density of the IMAT. The oven 152 for the high-pressure stage 150 is thermally designed so that no power is needed from the heater 162 during normal operation. The internal heating element 162 will be disabled after the warm-up (start-up) period. Heat generated from the IMAT's 160 during operation is used to keep the oven interior 158 at operating temperature.

A main controller 110 controls the operation of the two subsystems 100 and 150 and provides user interfaces. The main controller 110 can enable or disable the temperature controllers 114 and 182 and power supplies 112 and 184 based on the data received from the pressure switches 124 and 198 and the temperature controllers 114 and 182. The control method during start-up, charging, or stand-by periods are described in subsequent paragraphs.

During start-up, the main controller 110 enables both temperature controllers 114 and 182 for ramping the two ovens 104 and 152 up to operating temperatures (normally about 700 degrees C.). During this time, both IMAT power supplies 112 and 184 and the oven air supply fan 186 are disabled. When both ovens 104 and 152 reach the operating temperatures, the two subsystems 114 and 150 go to charging mode or period.

During the charging period, the main controller 110 first enables the low-pressure subsystem 100 operation to build up oxygen pressure to the point pressure switch PSW1 124 to change its state. After pressure builds in the low-pressure circuit 100, the main controller 110 starts disabling the internal heating element 162 in the high-pressure subsystem 150.

Temperature control in the high-pressure subsystem 150 will then be controlled using the high-pressure IMAT power supply (IMAT Power Supply 2) 184. The main controller 110 enables the IMAT power supply 2184 based on signals received from the oxygen pressure in the low-pressure circuit (PSW1) 124, oxygen pressure in the high-pressure circuit (PSW2) 198, and from the high-pressure oven temperature (Temperature Controller 2) 182.

The control logic methodology for IMAT power supplies and Oven Air Supply Fan are shown below. Note that PSW1 124 and PSW2 198 should preferably have large hystereses to avoid excessive cycling of the on/off control of the subsystems.

A preferred series of steps are as follows:

IMAT Power Supply 1 112 on=(PSW1 124 is below lower level (i.e. <50 psig)) AND (temperature is above minimum operating temperature)

IMAT Power Supply 1 112 off=(PSW1 124 is above higher level (i.e. >100 psig)) OR (temperature is below minimum operating temperature)

Oven Air Supply Fan 186 on=IMAT Power Supply 1 112 on.

IMAT Power Supply 2 184 on=(PSW1 124 is NOT below lower level (i.e. >50 psig)) AND (PSW2 198 is NOT above higher level (i.e. <=2000 psig)) AND (Oven 2 152 temperature is less than maximum operating temperature (i.e. <750 degrees C.)).

IMAT Power Supply 2 184 off=(PSW1 124 is below lower level (i.e. <50 psig)) OR (PSW2 198 is above higher level (i.e. >2000 psig)) OR (Oven 2 152 temperature is greater than maximum operating temperature (i.e. >750 degrees C.)).

After the charging period (PSW2 198 switched), the system goes to standby mode. In the standby mode, the low-pressure subsystem 100 is controlled by the same operating logic as shown above. However, the high-pressure main control purpose becomes to keep the oven 152 in operating temperature range without net increase in pressure. The IMAT power supply 2184 output polarities are cycled so that the IMAT's 160 generate heat without a net increase in oxygen charging pressure.

Alternatively, the low pressure subsystem 100 providing the input gas to the high pressure subsystem 150 can be a PSA type, rather than an electrochemical gas generator.

Alternative System Embodiments

The present oxygen generator with storage and conservation mode may include the following alternative embodiments:

1. Instead of cycling a solenoid valve to create the pulse of oxygen flow at the initiation of inhalation, the voltage being applied to the COG generator module(s) 14 can be cycled to produce the desired cycling flow to the individual or user. This embodiment would be beneficial in cases where system size is less critical or where pressurized oxygen storage is not desired. The overall system schematic could be simplified or reduced to a COG generator or system 14 connected electronically to an ECU 16 and pneumatically to the nasal cannula 32. The ECU 16 may also have sensor inputs from selected known design of sensors.

2. After a predetermined period of an essentially consistent breathing pattern, a software algorithm(s) embodied in the ECU 16 can begin to predict or anticipate the next breath, and further optimize the efficiency of the delivery of the oxygen to additionally reduce the oxygen consumption.

3. An alternative oxygen delivery sequence is to inject oxygen into the mask or cannula at the end of exhalation or into the mask hose immediately up stream of the mask inhalation check valve at the completion of inhalation to prepare for the next inhalation. This is an alternative to waiting for the detection of the inhalation sequence to begin, which may delay the system response and fail to provide oxygen at the most efficient point in the inhalation cycle.

4. Other sensors can be added to optimize the oxygen pulse modulation for ambient pressure and temperatures to provide the desired physiological protection.

5. During aircraft high G operation the optional separate anti-G valve can provide a pressure signal to activate the pressure breathing for G's (PBG) mode of the breathing regulator 28. The breathing regulator 28 will then use the stored oxygen that was generated by the COGS 14 to and add it to ambient air from the aircraft cabin to provide the desired oxygen concentration to meet the aircrew physiological needs.

6. Alternatively, an algorithm can be provided in an electronic controller for the breathing regulator 28 to provide added pressure control to combat the push-pull effect as taught in U.S. Pat. No. 6,450,943.

7. Use the stored oxygen during system start-up to provide oxygen requirements while system is in a warming sequence.

8. The heat energy being dissipated by the COGS 14 can be utilized as a source of heat for other needs, such as for aircrew comfort.

9. The present system can resort to a 100% mode by using the stored oxygen during exposure to CBW (chemical biological warfare).

10. Alternatively, the present system can provide oxygen to the ejection seat mounted emergency oxygen system (EOS) 44, which provides oxygen to the crewmember during ejection from the aircraft at the higher altitudes.

11. Alternatively, warm engine bleed air could be used to reduce the heat loss and the amount of insulation required to maintain the high temperatures inside the COGS oven.

12. The COG 14 could be replaced by any oxygen generator that can also deliver the oxygen at elevated pressures; such as a PSA-based OBOGS coupled with an oxygen compressor.

13. A known oximeter can be added to provide closed loop feedback that supports adjustment of the oxygen pulses or continuous flow to improve blood oxygen levels. An alarm can be initiated to allow manual decisions or automatic controls with patient notification alarm.

14. The controls can include an emergency mode that can be manually or automatically activated that increases the COG module 14 drive voltage above the normal voltage to increase the generation rate when demand exceeds the real-time generation rate and the storage has been depleted. An alarm can also be initiated.

15. The ECU 16 can be separated to reside with the ambulatory cylinder and the COG can be more simply controlled to just refill the cylinder(s)

16. For aviation oxygen applications an ambulatory cylinder can be added to provide a breathable supply for ingress and egress during CBW attacks.

17. For aviation oxygen systems a closed loop breathing system can be designed with a $CO_2$ scrubber to conserve oxygen and eliminate the need for filtered air to conserve oxygen.

The foregoing disclosure and description of the invention are illustrative and explanatory thereof, and various changes in the size, shape and materials, as well as in the details of the illustrated construction may be made without departing from the spirit of the invention.

What is claimed is:

1. A gas generating system comprising:
    an electrochemical oxygen generating unit for producing a controlled amount and pressure of a desired product gas using a ceramic membrane structure;
    an electronically controlled unit (ECU) controlling the operation of the electrochemical oxygen generating unit, said ECU being operably connected to said oxygen generating unit and to a first pressure transducer means for sensing inhalation demand;
    a second pressure transducer means operably connected to the ECU for sensing pressure in a storage unit and/or an ambulatory cylinder;
    a regulator means operably connected to said oxygen generating unit for controlling the product gas flow to a user of the product gas; and
    a pulsing valve that is operably associated with the ECU and the regulator means to provide a savings in product gas consumption.

2. A two stage ceramic gas generating system for generating a low pressure product gas and a high pressure product gas comprising:
    a low pressure gas generating subsystem comprising a ceramic membrane structure for generating the product gas at a selected low pressure; and
    a high pressure gas generating subsystem having an electrochemical oxygen generating system means using a separate ceramic membrane structure adapted to receive at least a portion of the low pressure product gas from the low pressure subsystem as an input stream to the ceramic membrane structure of the high pressure subsystem for generating the product gas at a desired pressure level greater than the pressure of the product gas from the low pressure subsystem.

3. The invention of claim 2 wherein the low pressure gas generating subsystem further includes an oxygen sensor operably mounted within an interior cavity of an oven for sensing oxygen concentration within the interior chamber and for generating a signal communicated to a control module controlling an input gas to the oven.

4. The invention of claim 2 wherein the low pressure gas generating subsystem further includes a separate second ceramic membrane structure for generating the product gas.

5. The invention of claim 2 wherein the low pressure gas generating subsystem is a pressure swing absorption (PSA) gas generator.

6. A high pressure gas generating system for producing a desired product gas comprising:
- a pressure vessel having an outer shell and an interior cavity adapted to contain a gas at a desired pressure and temperature and having an inlet for communicating an input gas to the interior cavity and an outlet for communicating the product gas from the interior cavity;
- a heating element within the interior cavity for adjusting the temperature of the interior cavity; and
- at least one electrochemical gas generating unit mounted within the interior cavity and adapted for purifying the selected input gas and producing the desired product gas; the electrochemical gas generating unit including a ceramic membrane structure subjected to a high pressure formed within the pressure vessel between the ceramic membrane structure and the outer shell of the pressure vessel;
- whereby the ceramic membrane structure is under compressive forces due to the high pressure formed within the pressure vessel.

7. The invention of claim 6 wherein the pressure vessel further includes insulation for retention of heat within the interior cavity.

8. The invention of claim 6 further including a controller operably connected to the heating element for adjusting the temperature in the interior cavity.

9. The invention of claim 6 wherein the temperature of the input gas is adjusted to a predetermined temperature state prior to being delivered to the ceramic membrane.

10. The invention of claim 6 wherein the relative composition of the input gas is pre-selected with reference to the desired product gas in order to reduce operating burden on the ceramic membrane unit during operation.

* * * * *